(12) United States Patent
Therin et al.

(10) Patent No.: US 8,142,515 B2
(45) Date of Patent: Mar. 27, 2012

(54) PROSTHESIS FOR REINFORCEMENT OF TISSUE STRUCTURES

(75) Inventors: Michel Therin, Lyons (FR); Philippe Gravagna, Irigny (FR)

(73) Assignee: Sofradim Production, Trevoux (FR)

( * ) Notice: Subject to any disclaimer, the term of this patent is extended or adjusted under 35 U.S.C. 154(b) by 981 days.

(21) Appl. No.: 10/690,625

(22) Filed: Oct. 23, 2003

(65) Prior Publication Data

US 2004/0138762 A1 Jul. 15, 2004

Related U.S. Application Data

(60) Provisional application No. 60/423,379, filed on Nov. 4, 2002.

(51) Int. Cl.
*A61F 2/02* (2006.01)
(52) U.S. Cl. .................... 623/23.72; 606/151
(58) Field of Classification Search .................. 424/445; 442/43; 602/43–50, 54–56; 606/151, 76–77, 606/214–215; 623/23.72, 23.73, 23.74, 23.75, 623/23.76, 1.11; 600/37
See application file for complete search history.

(56) References Cited

U.S. PATENT DOCUMENTS

| | | | |
|---|---|---|---|
| 4,603,695 A | 8/1986 | Ikada et al. | |
| 6,042,592 A * | 3/2000 | Schmitt | 606/151 |
| 6,162,962 A * | 12/2000 | Hinsch et al. | 623/11.11 |
| 6,406,423 B1 * | 6/2002 | Scetbon | 600/30 |
| 6,451,032 B1 * | 9/2002 | Ory et al. | 606/151 |
| 6,638,312 B2 * | 10/2003 | Plouhar et al. | 623/23.72 |
| 2003/0023316 A1 * | 1/2003 | Brown et al. | 623/23.72 |

FOREIGN PATENT DOCUMENTS

| | | | |
|---|---|---|---|
| EP | 0 774 240 A1 * | 11/1996 | |
| EP | 0 895 762 A2 | 2/1999 | |
| FR | 2 724 563 | 3/1996 | |
| WO | WO 02/078568 A1 * | 4/2002 | |

* cited by examiner

*Primary Examiner* — Melanie Tyson
(74) *Attorney, Agent, or Firm* — Carter, DeLuca, Farrell & Schmidt, LLP

(57) ABSTRACT

The present invention relates to a composite prosthesis for reinforcement of a tissue structure, including a porous textile support which includes an arrangement of threads each composed of at least one filament of nonabsorbable polymer material, said textile support defining a microporous texture including the interstices located between at least two threads at the sites of contact of one thread with at least one other thread, wherein, in at least one protected zone of the textile support, a hydrophilic absorbable material coats the textile support, forming a film enveloping and penetrating into the arrangement of threads, occluding at least the microporous texture, but without forming a plane layer covering at least one face of the textile support.

It also relates to a process for preparing such a composite reinforcement prosthesis.

12 Claims, 2 Drawing Sheets

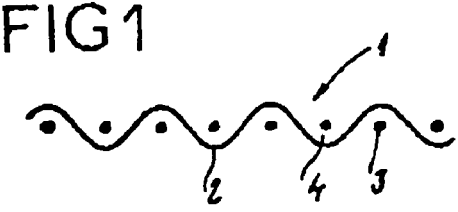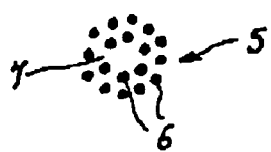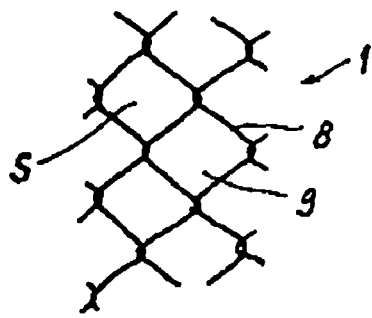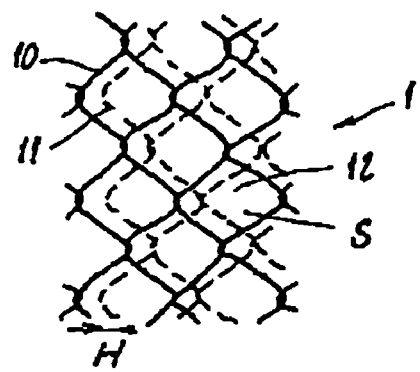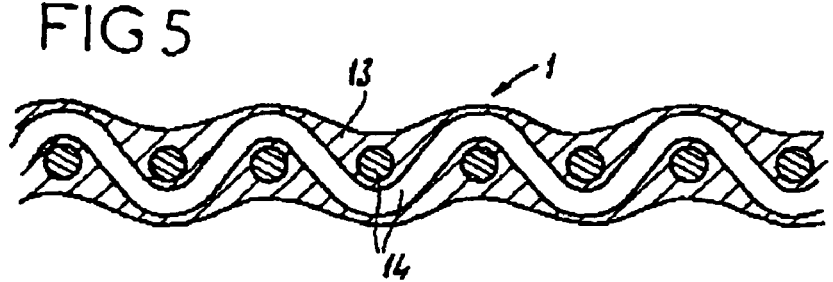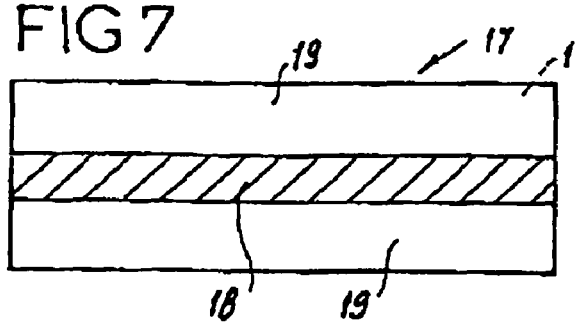

PROSTHESIS FOR REINFORCEMENT OF TISSUE STRUCTURES

This nonprovisional application claims the benefit of U.S. Provisional Application No. 60/423,379, filed Nov. 4, 2002.

FIELD OF THE INVENTION

The present invention relates to a prosthesis for reinforcement of tissue structures, in particular of tissues situated outside the peritoneal cavity and hence referred to as extraperitoneal.

Some organs, or parts of organs, in the human body, in particular the extraperitoneal organs situated in the pelvic cavity, for example the female urethra, bladder or rectum, may suffer an abnormal downward displacement generally called a prolapse or, more specifically, a cystocele in the case of the bladder or a rectocele in the case of the rectum. This displacement commonly occurs when the means fixing and supporting the organ grow slack. Persons skilled in this field also refer to these phenomena as pelvic floor disorders. Moreover, following hernias or eventrations of the abdominal wall, it is customary to perform surgery to treat the parietal defect. To do so, the surgeon usually employs reinforcement and support prostheses which are implanted at the desired site. These reinforcement prostheses are generally intended for permanent implantation and for this reason often consist, for example, of a textile support made of a nonabsorbable material.

Textile supports are intrinsically adhesiogenic and fibrotic irrespective of the nature of the tissues with which they are placed in contact. This property when considered with respect to support tissues (muscles, aponeuroses, fascias, etc.) in fact constitutes an indispensable prerequisite for the quality of the result. By contrast, with respect to other more fragile structures, the presence of a textile support at the initial phase of cicatricial inflammation promotes the creation of dense fibrous connections where previously there were only loose connections, such as those provided by the interstitial connective tissues for the extraperitoneal organs, and where there was no connection, for the intraperitoneal organs. For this reason, the porous nature of textile supports is often the cause of the development of postsurgical adhesions and erosions.

To overcome this problem, it has been proposed to make at least one face of these reinforcement prostheses completely smooth during the initial inflammatory phase, and hence unlikely to generate these adhesions.

DESCRIPTION OF THE PRIOR ART

Thus, WO99/06080 describes a porous textile support intended for use in parietal surgery, in the repair of eventrations or hernias, one face of which support is covered superficially by an absorbable plane layer or membrane, while the other face is left free for intimate and early tissue integration.

WO96/08277 describes a transparent collagenic membrane which can be deposited on both faces of a synthetic textile lattice.

Such reinforcements may represent satisfactory solutions in the field of intraperitoneal parietal surgery, which concerns an implantation site where there is rapid surface peritonealization, the newly formed peritoneum constituting the best protection of the organs potentially in contact. However, in surgical treatment for supporting tissues or for repairing prolapses, the surgeon may be dealing with extraperitoneal tissues which are particularly exposed since they can come into contact with both faces of the reinforcement, for example the vagina on one side and the rectum or bladder on the other, all the more so since they will not be protected in the long term by the formation of new peritoneum. These tissues are, for example, hollow viscera, such as the bladder, vagina, uterus or rectum, or natural ducts of the organism, such as the urethra, esophagus, trachea or blood vessels, or else nerves, tendons or the dura mater. For fragile tissues such as these, the fibrous connections subsequent to the initial cicatricial inflammation may be aggravated by erosion or fistulas which are always undesirable because they compromise the normal physiology of the structure concerned. In this case, it is necessary, during the initial phase of cicatrization, to protect these surrounding fragile tissues while at the same time permitting onset of cicatrization of the surrounding connective support tissues (fascia, aponeuroses, interstitial connective tissue), guaranteeing the long-term quality of the result of the reconstruction.

Moreover, as in any surgical procedure, the implantation of a nonabsorbable material into the human body poses certain risks of infection. Thus, it may happen that the material implanted is infected by perioperative contamination of the implantation site. This risk is all the greater since the recommendations concerning aseptic conditions in any surgical procedure are difficult to strictly implement, for example when using a vaginal approach. In this connection, it is known that the surface of nonabsorbable synthetic polymers promotes adhesion of bacteria. The adsorption or fixing of a bacterium onto a nonabsorbable support facilitates synthesis of a shell protecting the bacterium from the natural mechanisms of defense or antimicrobial mechanisms. Thus, for a given material, the greater the developed surface of the prosthesis, the more considerable the bacterial adhesion. However, adhesion of bacteria to a support is a condition triggering and facilitating their proliferation.

SUMMARY OF THE INVENTION

Thus, with a view to optimizing the surgical procedure consisting in implanting permanent reinforcement prostheses, in particular for supporting fragile tissues such as the extraperitoneal tissues, and in particular in environments where it is difficult to maintain strictly aseptic conditions, it would be particularly advantageous to be able to reduce as far as possible, during the initial phase of cicatrization, the developed surface of these prostheses which is accessible both to these surrounding fragile tissues and to possible bacteria. Thus, it would be desirable for these prostheses to have, at least during the initial phase of cicatrization, a surface which is as large as possible but is physically unfavorable to adhesion of bacteria and noninjurious to the surrounding tissues. Moreover, such a reinforcement would offer any bacteria present only a temporary biodegradable surface, thereby facilitating elimination of these bacteria by the competent cells.

The Applicant has found that a specific covering, namely a coating, of the developed solid surface of a textile support with an enveloping film of hydrophilic absorbable material was able to meet the requirements indicated above.

Thus, the present invention relates to a composite prosthesis for reinforcement of a tissue structure, comprising a porous textile support which includes an arrangement of threads each composed of at least one filament of nonabsorbable polymer material, said textile support defining a microporous texture comprising the interstices located between at least two threads at the sites of contact of one thread with at least one other thread, wherein, in at least one protected zone of the textile support, a hydrophilic absorbable material coats the textile support, forming a film enveloping and penetrating into the arrangement of threads, occluding at least the microporous texture, but without forming a plane layer covering at least one face of the textile support.

The present invention also relates to a process for preparing a composite prosthesis for reinforcement of a tissue structure, said process comprising the following steps:
 i) preparing a solution A of a hydrophilic absorbable material, in the fluid or liquid state,
 ii) impregnating at least part of the surface of a porous textile support with solution A, said porous textile support comprising an arrangement of threads each composed of at least one filament of nonabsorbable polymer material, said textile support defining a microporous texture which includes the interstices located between at least two threads at the sites of contact of one thread with at least one other thread,
 iii) drying the impregnated part of the textile support.

By virtue of the invention, that part of the textile support coated with the absorbable material is protected during the initial phase of cicatrization, that is to say it is not exposed to the inflammatory cells, such as granulocytes, monocytes, and macrophages, or the polynuclear giant cells generally activated by the surgical procedure. Nor is it exposed to the bacteria which may possibly be present. In fact, during the initial phase of cicatrization, the duration of which can vary from 5 to 10 days approximately, only the absorbable material is accessible to the various factors such as proteins, enzymes, cytokines, or the inflammatory cells.

Moreover, by virtue of the invention, during the period of digestion of the absorbable material, the surrounding fragile tissues, such as the hollow viscera for example, are protected in particular from the formation of severe and undesirable postsurgical fibrous adhesions.

Another advantage of the invention lies in the fact that it permits the onset of cicatrization of the surrounding connective support tissues, such as the fascias, aponeuroses, interstitial connective tissues, in contact with a hydrophilic and absorbable surface, itself favoring rapid development of a weakly inflammatory cellular covering. This onset of cicatrization of the surface in contact with the film of the prosthesis recreates a regular plane of organization of the fibrosis and of the cicatricial tissue, which fact facilitates subsequent restoration ad integrum of the tissues torn during the surgical procedure. Thus, after absorption of the film, the pores of the textile support are invaded directly by a tissue which is already partially freed from its inflammatory component.

The term "porous textile" as used in the present invention is to be understood as a textile support having empty spaces in the form of interstices and/or volumes. More precisely, the porous textile support is composed of an arrangement of threads defining a microporous texture and/or a macroporous texture.

The arrangement of threads in question is an interlacing which may be ordered, for example woven, according to any suitable weave, or knitted, or else unordered, for example nonwoven. In a preferred embodiment of the invention, the arrangement of threads constitutes a knitted structure. In such a case, the interstices located between at least two threads at the site of contact of one thread with at least one other thread belong to the meshes of the knitted structure. The empty spaces defined between the threads, away from their sites of contact, are the intermesh spaces of the knitted structure. Each thread in question comprises at least one continuous or noncontinuous filament made of nonabsorbable polymer material; each thread can comprise other threads or filaments, for example made of absorbable polymer material.

The term "polymer material" is to be understood as any material, alone or in combined form, comprising a synthetic or natural polymer obtained for example by polymerization or copolymerization. The nonabsorbable polymer material according to the invention can be a polypropylene or alternatively a polyester of the polyethylene terephthalate type.

The microporous texture comprises at least the interstices located between at least two threads at the sites of contact of one thread with at least one other thread. In the case where at least one thread comprises several filaments made of nonabsorbable polymer material, which may or may not be joined together, the microporous texture additionally comprises the interstices between filaments of the same thread.

The microporosity of the textile support can thus be defined as being the sum of i) the interstices, if any, located between at least two filaments within the same thread and ii) the interstices located between at least two threads at the sites of contact of one thread with at least one other thread.

The macroporous texture or macroporosity comprises the volumes whose surface S is defined by the empty spaces between at least two threads, away from their sites of contact, and whose height H is defined by the thickness of the textile support. According to the present invention, the textile support is considered as being flat when it constitutes a two-dimensional structure, preferably when its thickness is less than or equal to 5 times the mean diameter of the threads of which it is made up. This will give a two-dimensional macroporosity or two-dimensional macroporous texture. In the case where the textile support constitutes a three-dimensional structure, preferably when the thickness of the textile support is strictly greater than 5 times the mean diameter of the threads constituting the support, this will give a three-dimensional macroporosity or three-dimensional macroporous texture.

In a preferred embodiment of the invention, the textile support constitutes a two-dimensional structure.

The textile support is made of a nonabsorbable polymer material commonly used in surgery. This nonabsorbable polymer material is preferably chosen from the group comprising polypropylenes, polyesters such as polyethylene terephthalates, polyamides and/or their mixtures. In a preferred embodiment of the invention, this polymer material is polypropylene. Examples of a polypropylene-based textile support suitable for the present invention are the product sold under the brand name Parietene® by Sofradim, the product sold under the brand name Prolene® by Ethicon, or the product sold under the brand name Marlex® by Bard.

According to the invention, "protected zone" is defined as the zone of the textile support coated with the hydrophilic absorbable material. The hydrophilic absorbable material is preferably chosen from the group formed by the collagens, polysaccharides, and their mixtures. Among the collagens which can be used according to the invention, the following may be mentioned:
 1) collagen whose helix structure is at least partially denatured by heat, without hydrolytic breakdown, and whose method of preparation is described in WO99/06080,
 2) native collagen, unheated, formed into a film, with or without glycerin, crosslinked by gamma irradiation or by other means chemical or physical,
 3) and/or their mixtures.

Among the polysaccharides which can be used as absorbable hydrophilic material according to the invention, mention may be made of oxidized cellulose, hyaluronic acid, starch, chitosan, crosslinked dextrans and/or their mixtures. All these materials are well known to the person skilled in the art. An example of an oxidized cellulose suitable for the present invention is the product sold under the brand name Interceed® by Ethicon. An example of hyaluronic acid suitable for the present invention is the product sold under the brand name Hyalobarrier® by Fidia Advanced Biopolymers, or the product sold under the brand name Seprafilm® by Genzyme.

The hydrophilic absorbable material coats the protected zone of the textile support, forming a film enveloping and penetrating into the arrangement of threads, which occludes the microporous structure, in other words at least the microporosity of the support, but without forming a plane layer or thick membrane covering at least one face of the textile support. The film directly or indirectly coats at least each thread completely, forming a coating. Moreover, in the case where each thread of the support is formed by a single filament, the absorbable film fills and thus occludes all the interstices located between at least two threads at the sites of contact of one thread with at least one other thread. In the case where at least one thread comprises several filaments, which may or may not be joined to one another, the film fills and thus likewise occludes all the interstices between filaments of the same thread.

In a preferred embodiment of the invention, the film of absorbable material is noncontinuous and preserves the macroporous texture of the textile support. The film then coats each thread and leaves free the volumes defining the macroporosity. Thus, the reinforcement preserves a pronounced macroporosity for rapid mechanical anchoring and immediate cell recolonization. Such coating with a noncontinuous film also makes it possible to temporarily stiffen the reinforcement and facilitate its handling by the surgeon. This latter property is particularly advantageous in laparoscopic surgery.

The film of absorbable material preferably has a thickness of less than or equal to 500 microns, and still more preferably in the range of 10 to 100 microns.

In another embodiment of the invention, the film can also occlude the macroporosity of the textile support over at least part of the protected zone. According to the invention, "occluded zone" is defined as the part of the protected zone for which the macroporosity is occluded. In this occluded zone, the film fills and occludes the two-dimensional or three-dimensional volumes defining the macroporosity. It is therefore continuous. In a preferred embodiment of the invention, the film occludes the macroporosity of the textile support over the whole of the protected zone.

The protected zone can either cover the whole of the textile support or just part of this support.

In a preferred embodiment of the invention, the textile support is in the form of a rectangular part and the protected zone extends along a central band of this part. Such a prosthesis has zones for immediate attachment to permit effective suspension immediately upon implantation, by retraction of the interstitial connective tissues, fascias and aponeuroses at the free edges of the threads constituting the textile support, relatively fibrotic zones for stable mechanical anchoring at the unprotected part of the textile support, and zones of nonaggressive and minimally fibrotic integration at the protected central zone of the reinforcement.

By virtue of the invention, the practitioner can cut out bands of suitable geometry from the prosthesis and place them in such a way as to obtain a support which is nonaggressive, by virtue of the protected zone, with respect to the fragile tissue structures, and a rapid anchoring in the unprotected zones away from the fragile structures. By way of example, the bands cut out can have parallel straight edges, of adaptable length and width, or can have parallel edges curved in an arch, of adjustable length and width, or can have nonparallel edges bulged in a central region, to support the prolapsed structures on a large surface, and narrower at the ends in order to constitute suspension strips for anchoring.

BRIEF DESCRIPTION OF THE DRAWINGS

The present invention will be better understood by referring to the attached figures:

FIG. 1 is a cross-sectional view showing the microporous texture of a textile support composed of threads each having a single filament;

FIG. 2 is a cross-sectional view, on an enlarged scale, showing the microporous texture defined within a thread comprising several filaments;

FIG. 3 is plan view showing the macroporosity of a flat textile support,

FIG. 4 is a perspective view showing the macroporosity of a three-dimensional textile support;

FIG. 5 is a cross-sectional view of a textile support coated by the continuous film;

FIG. 6 is a cross-sectional view of a textile support coated with a noncontinuous film;

FIG. 7 is a plan view showing a reinforcement prosthesis of rectangular shape whose protected zone is in the shape of a central band;

DESCRIPTION OF THE PREFERRED EMBODIMENTS

Figure 8:
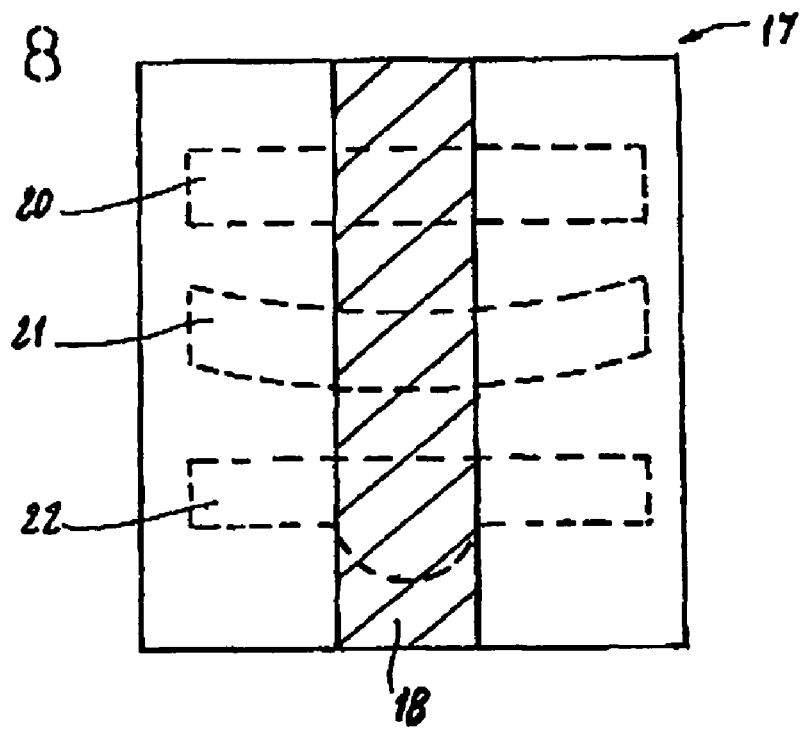
FIG. 8 is a plan view of the prosthesis from FIG. 7 showing different shapes of bands cut from the prosthesis.

Referring to FIG. 1, a textile support of the porous tissue type 1 is shown, comprising weft threads 2 and warp threads 3. The interstices 4 defined in this case between the threads constitute the microporous texture.

FIG. 2 shows a cross section of a thread 5 comprising several continuous or noncontinuous filaments 6 joined to one another, for example by twisting. The interstices 7 defined between the filaments 6 within the thread 5 also constitute a microporous texture.

FIG. 3 shows knitted threads 8 constituting a two-dimensional textile support 1. The volumes 9 whose surface S is defined by the empty space between at least two threads away from their sites of contact, and whose height H is less than about 5 times the mean diameter of the threads 8, constitute a two-dimensional macroporous texture.

FIG. 4 shows a three-dimensional textile support 1 composed of threads 10 constituting a first knitted (or woven) plane layer and threads 11 constituting a second knitted (or woven) plane layer parallel to the first one, and separated by a height H; the first and second layers are connected to one another by knitted loops for example. The volumes 12 whose surface S is defined by the empty space between at least two threads away from their sites of contact and of height H constitute a three-dimensional macroporous texture.

FIG. 5 shows a textile support 1 which is coated with a continuous film 13 and whose threads 14 are made up of monofilaments.

FIG. 6 shows a textile support 1 composed of threads 15 with a single filament and coated by a noncontinuous film 16. Each filament is coated by the film 16. The empty spaces between the filaments remain free.

FIG. 7 shows a reinforcement prosthesis 17 of rectangular shape whose protected zone 18 represents a central band, while the lateral parts 19 of the textile support 1 are not protected.

FIG. 8 shows a reinforcement prosthesis 17 of rectangular shape whose protected zone 18 is in the shape of a central band, on which prosthesis we have shown the shapes corresponding to:

- a strip 20 with parallel edges, of which the central part is a protected zone,
- a strip 21 with parallel edges curved in an arch, of which the central part is a protected zone,
- a strip 22 with nonparallel edges, of which the bulged central part is a protected zone and of which the narrower lateral parts are nonprotected.

These strips can be cut out by the surgeon directly at the operating site and in themselves constitute prostheses according to the invention.

A composite reinforcement prosthesis according to the invention can be prepared in accordance with the process comprising the following steps:

i) preparing a solution A of a hydrophilic absorbable material, in the fluid or liquid state,
ii) impregnating at least part of the surface of a porous textile support with solution A, said porous textile support comprising an arrangement of threads each composed of at least one filament of nonabsorbable polymer material, said textile support defining a microporous texture which includes the interstices located between at least two threads at the sites of contact of one thread with at least one other thread,
iii) drying the impregnated part of the textile support.

The process for preparing the prosthesis according to the invention is simple and rapid. Thus, it comprises only a single step of impregnating that part of the textile support which is to be protected. The impregnation step can be done by immersing said part of the surface of the textile support in solution A or by spraying the solution A onto said part of the surface of the textile support, preferably with the aid of a stencil or protective mask. The impregnation solution A must be sufficiently fluid so that it impregnates the textile support in order to occlude the microporosity. This solution can be heated to a temperature below 50° C. In order to facilitate this impregnation step, solution A preferably has a viscosity of less than or equal to 1000 centipoises, and still more preferably from 50 to 200 centipoises, this viscosity being measured with the aid of a CONTRAVES-TV viscosimeter, for example, at the chosen temperature of less than 50° C. Those parts of the textile support which are not intended to be coated can be covered with a protective membrane during impregnation step ii). In the case where the coated zone represents a central band of the textile support, the support can also be folded beforehand into a U shape, the part to be coated being the horizontal bar of the U, and the part to be coated can thus be immersed in solution A while preserving the lateral parts (vertical bars of the U).

In the case where the whole of the textile support is to be coated, the textile support is simply immersed in its entirety in solution A and then allowed to dry. The protected zone thus has a surface entirely covering that of the textile support.

The impregnation step can be repeated if one wishes to increase the quantity of coated material.

The impregnated part of the textile support can be dried by leaving the support resting in a flow of clean air at ambient temperature or in a thermostated chamber at a maximum temperature adapted to the absorbable substance, for example less than or equal to 30° C. for collagen, less than or equal to 60° C. for polysaccharides.

Thus, the reinforcement prosthesis according to the invention can be produced by first cutting a textile support to the desired shape and dimensions, then coating it completely or partially using the process described above, in order to obtain the final prosthesis which is to be implanted in the body of the patient.

Another way of producing a prosthesis according to the invention is to first coat a part, for example a central band, of a textile support of given shape, for example rectangular, using the process described above, for example by folding the support in a U shape, and then cutting from this partially coated support a prosthesis of defined geometry so that in its final configuration this prosthesis has, for example, a protected central zone and nonprotected lateral zones for immediate attachment.

The reinforcement prosthesis according to the invention can be applied to any tissue structure of the body. This tissue structure is preferably an extraperitoneal tissue.

EXAMPLE 1

Figure 9:
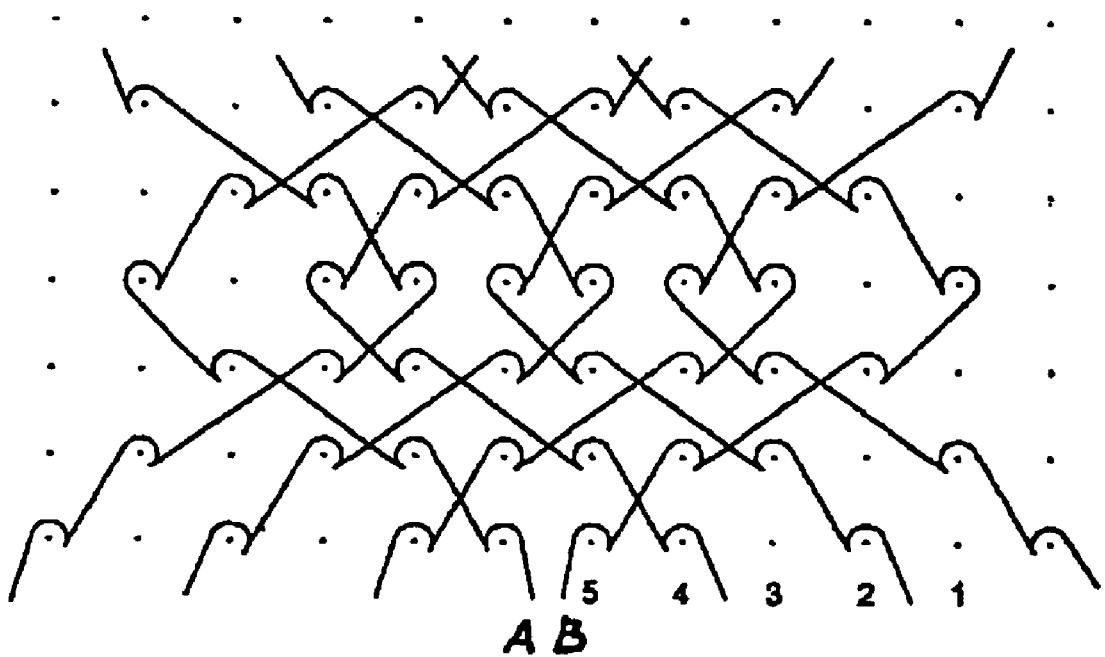
FIG. 9 shows a diagram of the knitting weave of a textile support suitable for the present invention.

A textile support is produced in which the arrangement of threads constitutes a knit formed by warp knitting of two plies of threads, according to the diagram in FIG. 9. In this figure, each ply of threads is identified by a letter, A or B, the diagram itself using a system of description of the knit which is entirely familiar and intelligible to the person skilled in the art, and which will not be described in detail here. The textile support is knitted on a warp-knitting machine with two guide bars.

The two bars corresponding to the threads A and B are threaded—one bar full, one bar empty—and move symmetrically so as to obtain staggered apertures. The final textile support can then be stabilized simply by passing it through an oven at a temperature of between about 110° C. and about 150° C.

The threads are polypropylene monofilaments whose diameter can vary from 0.08 to 0.18 mm.

The textile support thus prepared using a thread of 0.10 mm in diameter has the following physical and mechanical characteristics: its weight is 38 g/m$^2$, its thickness is 0.4 mm, the mean surface area of the pores, measured by optic or electron microscopy, is 1.5×1.7 mm$^2$, the mean porosity, measured by calculating the ratio between the density of the constituent material and the total volume of the textile, is 89%, the resistance to rupture, measured according to ISO13934-1, is 146 N for warp and 146 N for weft, the tear strength, measured according to ISO4674-A2, is 26 N for warp and 23.6 N for weft, the bursting strength, measured according to ISO13938-1, is 617 Kpa, the elasticity at 10 daN, expressed as a percentage of deformation under the indicated load (10 daN) in the test according to ISO13934-1, is 53% for warp and 62% for weft.

It is possible to integrate, within this textile, zones obtained by knitting with different threads and/or weave in such a way as to obtain zones with physical characteristics (size of pores, density, thickness) and mechanical characteristics (resistance to curling, elasticity) adapted to the present invention.

A solution is prepared comprising collagen modified by oxidative cutting and heating, polyethylene glycol and glycerin. The weight concentrations of collagen, polyethylene glycol and glycerin are preferably respectively between about 2 and 9% for the collagen, between about 0.6 and 3% for the polyethylene glycol, and between about 0.3 and 1.2% for the glycerin.

This solution has a viscosity of from 50 to 200 centipoises. A central band of the textile support is immersed in this solution, then it is withdrawn and left to gel for 30 minutes. This operation is repeated as many times as is necessary to obtain a film with a density of 0.133 g/cm$^2$.

After maturation, the whole arrangement is sterilized with ethylene oxide.

A textile support is obtained whose central band is occluded.

EXAMPLE 2

Starting from the same textile support and the same solution as were described in Example 1, the solution is sprayed onto the central band of the textile support which is to be protected. The spraying is carried out on one face of the textile. After 30 minutes of maturation of the gel formed on the surface of the textile, the solution is sprayed onto the other face. After the second spraying operation, the whole arrangement is left to dry under a flow of sterile air. The quantity of solution necessary to obtain a film with a final density of 0.133 g/cm$^2$ is sprayed on. After maturation, the whole arrangement is sterilized with ethylene oxide.

An intermediate composite part is obtained whose central band is an occluded zone according to the invention and whose lateral parts are devoid of absorbable material.

The invention claimed is:

1. A composite prosthesis for reinforcement of a tissue structure, comprising a porous textile support which includes an arrangement of threads each composed of at least one filament of nonabsorbable polymer material, the textile support having at least one protected zone and at least one nonprotected zone, the textile support defining a microporous texture comprising interstices located between at least two threads at sites of contact of one thread with at least one other thread, wherein the microporous texture in the at least one protected zone of the textile support is occluded by a hydrophilic absorbable material which coats the textile support, forming a film enveloping and penetrating into the arrangement of threads, and the microporous texture in the at least one nonprotected zone of the textile support is not occluded, the textile support further defining a macroporous texture comprising volumes whose surface is defined by the empty spaces between at least two threads away from the sites of contact, and whose height is defined by a thickness of the textile support, and wherein the macroporous texture of the textile support in a first portion of the protected zone is not occluded by the film and the macroporous texture of the textile support in a second portion of the protected zone is occluded by the film.

2. The prosthesis as claimed in claim 1, wherein the textile support constitutes a two-dimensional structure.

3. The prosthesis as claimed in claim 1, wherein the film has a thickness of less than or equal to 500 microns.

4. The prosthesis as claimed in claim 3, wherein the film has a thickness from 10 to 100 microns.

5. The prosthesis as claimed in claim 1, wherein at least one thread comprises several filaments of nonabsorbable polymer material, and the microporous texture additionally comprises the interstices between filaments of the same thread.

6. The prosthesis as claimed in claim 1, wherein the textile support has the shape of a rectangular part and the protected zone extends along a central band of the rectangular part.

7. The prosthesis as claimed in claim 1, wherein the textile support is in the shape of a strip with parallel edges, the central part being a protected zone.

8. The prosthesis as claimed in claim 1, wherein the textile support is in the shape of a strip with parallel edges which are curved in an arch, the central part being a protected zone.

9. The prosthesis as claimed in claim 1, wherein the textile support is in the shape of a strip with nonparallel edges having a bulged central part and narrower lateral parts, wherein the bulging central part includes the protected zone and the narrower lateral parts being nonprotected.

10. The prosthesis as claimed in claim 1, wherein the absorbable material is chosen from the group formed by collagens, polysaccharides, and their mixtures.

11. The prosthesis as claimed in claim 1, wherein the tissue structure is an extraperitoneal tissue.

12. A composite prosthesis for reinforcement of a tissue structure, comprising
a three-dimensional knitted structure which includes an arrangement of at least a first nonabsorbable thread and a second nonabsorbable thread,
the knitted structure defining a microporous texture comprising interstices located at sites of contact of the first nonabsorbable thread and the second nonabsorbable thread,
the knitted structure further defining a macroporous texture comprising empty spaces between the sites of contact of the first nonabsorbable thread and the second nonabsorbable thread,
the three-dimensional knitted structure having a protected zone, a nonprotected zone and a height defined by a thickness of the knitted structure; and
a hydrophilic absorbable material positioned on at least a portion of the knitted structure to form the protected zone,
wherein the microporous texture in the protected zone is occluded by the hydrophilic absorbable material, and the microporous texture in the nonprotected zone is not occluded,
wherein the macroporous texture of the knitted structure in a first portion of the protected zone is not occluded by the hydrophilic absorbable material and
the macroporous texture of the knitted structure in a second portion of the protected zone is occluded by the hydrophilic absorbable material.

* * * * *